United States Patent [19]

Mälson et al.

[11] Patent Number: 4,716,154
[45] Date of Patent: Dec. 29, 1987

[54] GEL OF CROSSLINKED HYALURONIC ACID FOR USE AS A VITREOUS HUMOR SUBSTITUTE

[75] Inventors: Tomas Mälson; Bengt L. Lindqvist, both of Uppsala, Sweden

[73] Assignee: Pharmacia AB, Uppsala, Sweden

[21] Appl. No.: 844,388
[22] PCT Filed: Jun. 7, 1985
[86] PCT No.: PCT/SE85/00239
§ 371 Date: Dec. 3, 1985
§ 102(e) Date: Dec. 3, 1985
[87] PCT Pub. No.: WO86/00079
PCT Pub. Date: Jan. 3, 1986

[30] Foreign Application Priority Data
Jun. 8, 1984 [SE] Sweden .............................. 8403090
[51] Int. Cl.$^4$ ............................................. A61K 31/70
[52] U.S. Cl. ..................................................... 514/54
[58] Field of Search ............................ 514/54; 536/41

[56] References Cited

U.S. PATENT DOCUMENTS 4,141,973  2/1979  Balazs .................................... 514/54
4,152,170  5/1979  Nagase et al. ....................... 536/1.1

OTHER PUBLICATIONS

Laurent et al, *Acta Chemica Scandinavica*, vol. 18, p. 279, 1964.

Primary Examiner—J. R. Brown
Assistant Examiner—Elli Peselev
Attorney, Agent, or Firm—Fred Philpitt

[57] ABSTRACT

The invention is concerned with a vitreous humor substitute intended for ophthalmological uses and consisting of a gel of crosslinked hyaluronic acid and a method at retinal surgery and after vitrectomy when the vitreous humor completely or partially is exchanged for such a gel.

16 Claims, No Drawings

GEL OF CROSSLINKED HYALURONIC ACID FOR USE AS A VITREOUS HUMOR SUBSTITUTE

This invention is concerned with a substitute for vitreous humor to be used in ophthalmology, consisting of a gel of crosslinked hyaluronic acid, and a method at retinal surgery and after vitrectomy when the vitreous humor completely or partially is exchanged for such a gel.

The vitreous humor of the eye, also known as "vitreous body", is a transparent gel-type material occupying an intraocular space which extends forward from the retina to the lens and ciliary body, these latter two formning (normally) the frontal boundary of said space while the retina forms the rear boundary. The retina comprises two layers which are not organically connected with each other over their entire area. The layer immediately adjacent to the vitreous humor, i.e. the receptor layer, contains photosensitive cells while the layer adjacent to the choroid consists of pigment epithelial cells. If fluid penetrates through the receptor layer this may result in a separation of the two layers, that is, in detachment of the retina. Usually this will occur when a hole has been torn in the retina and morbid changes have occurred in the vitreous humor.

Treatments in cases of retinal detachment imply closing the rupture by means of for example a coagulation method such as e.g. cryopexy and contacting the detached retina with the pigment epithelial layer and the choroid. This latter step may be carried out by means of an inward buckle impressed from the outside on the sclera and choroid, or by means of injection of some substance that will increase the volume of the vitreous humor and thereby increase the pressure exerted by the vitreous humor on the retina.

For this last-mentioned method, a number of substances have been tried as substitutes for vitreous humor in cases where recourse has been had to vitrectomy (complete or partial removal of the vitreous humor by surgery) as e.g. after hemorrhages that have not been resorbed satisfactorily or after membrane ingrowth with concomitant retinal detachment due to traction. Examples of such substances are: Gases, salt solutions, silicone oil, polyvinyl pyrrolidone, hyaluronic acid, and hydrogels of the polyacrylamide type as well as polyglyceryl methacrylate.

An ideal vitreous humor substitute will have to possess a high degree of transparency and about the same refractive index as the vitreous humor. The substitute has to be a non-toxic, non-inflammatory, non-immunogenic substance. Moreover, it must be a substance that can be applied easily, for example by injecion through a fine needle tip, without undergoing any deterioration of its properties while being thus applied; and in some cases a further requirement is that this substance should be capable of controllable swelling. This substance may be required to act as a support during a prolonged period of time and should therefore be a material—preferably gel material—that is not easily degraded or decomposed. In cases of retinal detachment, a complication occurring fairly often is that secondary reactions show up in the form of cellular growth, concomitant membrane formation and traction forces exerted on the retina. It is therefore a highly important requirement that the substitute material introduced should not be a cell growth substrate.

The aforesaid vitreous humor substitutes of the prior art have serious drawbacks in one or more respects. Thus for instance, silicone oil while being an efficient substance for promoting attachment of the retina has a high frequency of side effects in the form of cataract formation, glaucoma and toxic effects on the tissues of the eye. Among the gaseous substitutes, the one that has been employed most commonly and for many years is air—which however, like several other low molecular substances tested, has the disadvantage of being eliminated too quickly so that consequently the retina is not held in a fixed position long enough for effective healing. Hyaluronic acid is a substance normally present in the eye; therefore injection of hyaluronic acid will not give rise to any toxicological or immunological reactions. However despite the fact that hyaluronic acid is a high molecular, high viscosity substance the duration of its tampon effect is not sufficient for treatment of the more severe cases of retinal detachment: The hyaluronic acid will become inefficient too soon for such severe cases, due to being dissolved in the aqueous humor and thus carried away.

We have now found that a gel of cross-linked hyaluronic acid has properties in very close agreement with those set forth above as characteristics of an ideal vitreous humor substitute.

The present invention therefore provides a gel of cross-linked hyaluronic acid to be used as a vitreous humor substitute, a method for producing such a gel and furthermore provides a method at retinal surgery and after vitrectomy, implying that a sterile and pyrogen-free gel of cross-linked hyaluronic acid is introduced into an intraocular space enclosed between a rear boundary formed by the retina and a frontal boundary normally formed by the lens and the ciliary body, the introduction of said gel being effected in a manner such that said gel (together with remaining natural vitreous humor, if any) will fill out all of said intraocular space. In eyes where the lens has been removed, so-called aphakic eyes, the frontal boundary of said space is formed by the cornea.—The gel of the present invention is used also in the treatment of retinal detachment, implying that a sterile and pyrogen-free gel of cross-linked hyaluronic acid is introduced into the aforesaid space enclosed between a rear boundary formed by the retina and a frontal boundary normally formed by the lens and ciliary body; this has the effect that the pressure applied on the receptor layer by the hyaluronic acid gel, conjointly with remaining portions of natural vitreous humor (if any), will cause the receptor layer to lie in contact with the pigment epitheial layer for a period of time sufficient for healing.

Gels of crosslinked hyaluronic acid for gel filtration have been described by Laurent et al. (Acta Chemica Scandinavica 18 (1964), 274–275). Schmut et al. have stated (Graefes Arch Clin Exp Ophthalmol 218 (1982), 311-314) that they have been the first to successfully produce stable gels from hyaluronate solutions at physiological pH, but that the hyaluronic acid —$Cu^{2+}$ gels are unsuitable for ophthalmological applications, inter alia because of the toxicity of the copper ion.

Hyaluronic acid is a highly viscous glucosamino glycan occurring naturally in animal and human tissues and having a molecular weight usually varying within the range of 20 000 to 8 000 000 depending on its source and purification method. However the molecular weight of the hyaluronic acid is not a critical factor for the practice of this invention, it being an easy matter in each individual case to properly adapt the concentration, type of crosslinking agents employed and degree of crosslinking to the molecular weight of each particular starting material. If for instance the hyaluronic acid has a low molecular weight then both the hyaluronic acid and its crosslinking agent will be added in higher concentrations than in cases where this starting material has a high molecular weight. According to a preferred embodiment a comparatively high molecular hyaluronic acid is chosen, its molecular weight being within the range of from 500 000 to 3 000 000. An important point to be noted is that the hyaluronic acid must have been purified from components that might otherwise cause toxicological or immunological reactions. It is recommendable to employ a highly purified product such as described in for example the U.S. Pat. No. 4,141,973.

Crosslinking according to the present invention is carried out with known bi- or polyfunctional crosslinking reagents which will produce stable bonds, e.g. ether or amide bonds. There are a large number of commercially available reagents for crosslinking hydroxyl-containing substances such as e.g. polysaccharides, all of these reagents having been described in the literature and being well known to persons skilled in the art. Preferred crosslinking reagents are bi- or polyfunctional epoxides, e.g. lower aliphatic epoxides, or their corresponding halohydrins or epihalohydrins or halides, in as much as these will form ether bridges to the hyaluronic acid molecules. As suitable examples may be mentioned epichlorohydrin, divinylsulfone, 1,4-butanediol diglycidyl ether, 1,2-ethylenediol diglycidyl ether, 1-(2,3-epoxypropyl)-2,3-epoxy cyclohexane, N,N-diglycidyl aniline (Leuktherm X50 Bayer) and epoxy-substituted pentaerythritol (Shell 162). Other crosslinking agents that may be employed are reactive polymers such as for instance dextran or starch which have been reacted to contain e.g. glycidyl ether groups. Products suitable for use in accordance with the present invention are obtained by carrying out the crosslinking reaction with the crosslinking agent in an amount corresponding to a molar ratio of about 0.03 to 4.0 per disaccharide repeating unit in the hyaluronic acid molecule.

The hyaluronic acid or a salt thereof such as for example the sodium salt is dissolved and reacted with the crosslinking agent in an alkaline medium for a period of time appropriate for the reaction; this is usually a couple of hours. Optionally the reaction may be performed at an elevated temperature, about 50° C. The gel of crosslinked hyaluronic acid will contain some residual unreacted crosslinking agent, and it is therefore of the utmost importance that the gel be washed very thoroughly, as for example by boiling in phosphate-buffered physiological saline.

The swollen gel has a very high content of liquid; these hyaluronic acid gels are perfectly homogeneous and transparent, having a refractive index in very good agreement with that of natural vitreous humor. Their high degree of transparency permits slit lamp examinations, as well as the use of photocoagulation techniques for retina fixation. A composition suitable for administration is a gel completely or partially swollen in phosphate-buffered physiological saline and having a concentration which corresponds to a solids content within the range of 0.1 to 50% by weight. These gels may be employed whole or crushed. A finely divided gel having a solids content of from 0.1 to 2.5% by weight, preferably 0.2 to 1.5% by weight, can be readily injected through a 0.9 mm needle tip. Such a gel will fill out the space into which it has been injected, to thus form therein a clear, optically homogeneous mass. It is also possible to employ a whole gel globule which has been shrunk and has a dry solids content of between 10 and 50% by weight, preferably 12 to 25% by weight, this globule being introduced surgically into the space normally occupied by the vitreous body. Then, by means of controlled swelling and due to its capacity of plastic deformation, the globule will fill out the entire free space; to do this it must be able to swell to a diameter of up to about 20 mm in case a complete vitrectomy has been carried out. To effect shrinking of the gel globule methods like e.g. drying in a gas stream may be used, to thus reduce the size of the globule to a dimension suitable for its introduction into the eye—i.e. a diameter of usually less than 6 mm.

Compositions containing a gel of crosslinked hyaluronic acid may of course be produced in many different ways by mixing the gel with components that will not cause any undesired reactions of the aforesaid kind. Thus for instance it will be readily appreciated that in addition to the hyaluronic acid gel the composition may contain other polysaccharides such as e.g. dextran, as well as compounds closely related to hyaluronic acid like chondroitin sulfate. Components of these types may be present also when the crosslinking reaction is carried out.

The gels are thermostable and can be liberated completely, by washing and heat treatment, from all traces of crosslinking reagents; and they can be sterilized by autoclaving.

The invention will be illustrated further by the below examples which however do not limit the scope thereof in any respect.

EXAMPLES

Preparation of hyaluronic acid gels

EXAMPLE 1

400 mg of sodium hyaluronate (molecular weight about $3 \times 10^6$) was dissolved in 3 ml of 1% sodium hydroxide in a plastic tube. After about half an hour 25 $\mu$l of 1,4-butanediol diglycidyl ether (BDDE) was added. The tube was centrifuged to produce a homogeneous solution. The tube was then heated to 50° C. for two hours, whereupon it was left standing overnight at room temperature. The gel that had formed was cut into small pieces and was washed thoroughly during a 24-hr period with distilled water to which acetic acid had been added. After further washing for 8 hrs by boiling in phosphate-buffered physiological saline (0,276 g $Na_2HPO_4.2H_2O$; 0.0395 g $NaH_2PO_4.H_2O$; 8.476 g NaCl per 1000 ml pH 7.3) the gel was drained, crushed to a desired particle size, and filled into syringes which were autoclaved.

The dry solids content of the gel (% of swollen gel in buffer) was 0.37%.

The epoxide content (BDDE std) was <1 ppm as determined on hyaluronidase-degraded gel that had been reacted with nicotinamide according to Nelis and Sinsheimer, Anal. Biochem. 115 (1981), 151–157.

The refractive index in phosphate-buffered physiological saline was 1.3350.

EXAMPLE 2

The gel was prepared as in Example 1, but with 40 μl of BDDE. The resultant gel had a solids content (% of swollen gel in buffer) amounting to 0.66%.

The epoxide content (BDDE std) was <1 ppm.

The refractive index in phosphate-buffered physiological saline was 1.3352.

As has been mentioned before, gels of hyaluronic acid may be prepared with varying amounts of crosslinking agents, hyaluronate and hydroxide. Other reaction parameters such as e.g. time and temperature may also be varied to achieve favorable gel forming conditions.

The reaction of Example 1 was repeated in a test series where the temperature, time, hyaluronate concentration, hydroxide concentration or amount of BDDE was varied while all the other parameters were kept constant.

Results:

| Temperature | | Time | |
|---|---|---|---|
| 25° C. | no gel | 15 min. | no gel |
| 50° C. | gel | 2 hrs | gel |
| 75° C. | no gel | 4 hrs | gel |
| 100° C. | no gel | 9 hrs | gel |
| Conc. of hyaluronic acid | | Conc. of hydroxide | |
| 2.5% | no gel | 0.1% | no gel |
| 5% | no gel | 1% | gel |
| 13.3% | gel | 3% | no gel |
| 20% | gel | 6% | no gel |
| Amount of BDDE | | | |
| 5 μl | | no gel | |
| 10 μl | | no gel | |
| 50 μl | | gel | |
| 100 μl | | gel | |
| 500 μl | | gel | |

While these data may give the reader a general idea as to what sorts of reaction conditions are generally suitable it will be appreciated that for persons skilled in the art it is an easy matter to effect changes in any combinations of two or more parameters in order to obtain the desired conditions of reaction (gel formation).

EXAMPLE 3

400 mg of low molecular sodium hyaluronate ($M_w$ about 20 000) was dissolved in 1 ml of 1.3% sodium hydroxide; then 300 μl of BDDE was added. The reaction was allowed to proceed for two hours at 50° C., whereupon the gel was washed as described above. In this case a gel of 1.2% solids content was obtained.

EXAMPLE 4

800 mg of sodium hyaluronate ($M_w$ about $1 \times 10^6$) was dissolved in 3 ml of 1% sodium hydroxide. 50 μl BDDE was added, and when the reaction had proceeded for 2 hours at 50° C. the product was washed as described above. A soft gel of 0.23% solids content was obtained.

EXAMPLE 5

400 mg of sodium hyaluronate ($M_w$ about $3 \times 10^6$) was dissolved in 3 ml of 1.3% sodium hydroxide, whereupon 70 μl of epichlorohydrin was added. The reaction was allowed to proceed for 2 hours at 50° C., the product then being washed as described above. The reaction in this case gave a gel of 0.9% solids content.

EXAMPLE 6

200 mg of sodium hyaluronate ($M_w$ about $3 \times 10^6$) was dissolved in 1.5 ml of 1% sodium hydroxide, whereupon 5 μl of divinyl sulfone was added. The mixture was left standing overnight at room temperature. After washing in the manner as described above a brittle gel was obtained; solids content 0.8%.

EXAMPLE 7

50 g of hyaluronic acid gel (produced according to Example 2) in distilled water was introduced into a dialysis tube which was then sealed. The tube was suspended and air-dried in that position. After 3 days the gel weight had decreased to 5 g. Upon resuspension in phosphate-buffered physiological saline the gel was seen to swell, during 24 hours, so as to occupy a volume of 7.5 ml; this was equivalent to 50% swelling.

EXAMPLE 8

1,200 ml of crushed hyaluronic acid gel (produced according to Example 2) in phosphate-buffered physiological saline was introduced into a pressure vessel; the vessel had a permeable bottom plate onto which an ultrafiltration membrane had been placed (Amicon Diaflo ® XM100A). 840 ml of liquid was expressed from the gel with the aid of applied gas pressure (3.5 kg/sq.cm). The gel was crushed to a finely divided state, filled into syringes and autoclaved. This gel could be readily extruded through a cannula of 0.8 mm interior diameter. To 20 ml of the partially swelled gel was added an excess of phosphate-buffered physiological saline which caused the gel to swell further to a 53 ml volume within 5 days.

EXAMPLE 9

9.3 g of hyaluronic acid gel (produced according to Example 2) in phosphate-buffered physiological saline was suspended in 5M sodium chloride solution. After 24 hours the weight of the gel had decreased to 7.7 g (83% of its original weight). The gel was then packed onto a column the volume of which was adapted to the gel volume. The column was eluted with physiological phosphate buffer until the gel was equilibrated therewith. When the gel was resuspended in the buffer it swelled again during a 24 hr period so as to reacquire its original weight (9.3 g).

EXAMPLE 10

400 mg of sodium hyaluronate ($M_w$ about $3 \times 10^6$) was dissolved in 3 ml of 1% sodium hydroxide. 100 μl of BDDE was added. Drops of the solution were portioned out into small polyethylene tubes containing 3 ml of a mixture of ethylene dichloride and toluene (61% ethylene dichloride, 39% toluene, v/v). The density of the hyaluronate solution was the same as that of the surrounding solvent mixture, and consequently the globules of hyaluronic acid that were now formed remained freely suspended in the solvent. The tubes were heated at 50° C. for 2 hours and were then left standing overnight. The gel globules were washed with distilled water followed by physiological phosphate buffer. One of these gel globules (weight 2.4 g) in phosphate-buffered saline was equilibrated with distilled water and dried in an air stream so as to reduce its weight to 140 mg. The dried and shrunken globule was then allowed to swell in said buffer; after 72 hours it had reacquired its original volume and weight.

Cell culture on hyaluronic acid gel

EXAMPLE 11

Human fibroblasts (line Flow 2002), primary heart fibroblasts and an epithelial cell line (VERO) were employed in these experiments, the culture medium being DME/F10 (80:20) with additions of 2 mM L-glutamine, 1% non-essential amino acids and 10% FCS. Disks of the gels (the latter having been prepared in the form of plates) were cut out and placed into bacteriological petri dishes; and the culture medium was added together with about 50 000 cells/dish. The cultures were incubated in a humid atmosphere at 30° C. (5% $CO_2$).

Readings of the dishes were performed every 24 hours during one week. On each occasion the numbers of attached cells and spread-out cells were recorded. Normal cell culture dishes were used as controls.

The results show that cells are unable to grow on hyaluronic acid gel in an in vitro situation, and that this applies to all kinds of cell types. They can attach but cannot spread out/proliferate or divide.

Crosslinked hyaluronic acid gel employed as vitreous humor substitute in vitrectomized rabbits

EXAMPLE 12

The rabbits (albino, Swedish loop, ) were anesthesized with Mebumal-vet. (ACO), 60 mg/ml diluted 1:3. The pupils were dilated using Mydriacyl 0.5% (Alcon) and Cyklogyl® 1% (Alcon). Tetracain (Alcon) was employed as local anasthetic.

After disengagement of the conjunctiva and attachment of a holding suture in the rectus nasalis a cut of 1.5 mm length was prepared 2 mm below the limbus, whereupon a 5-0 Mersilene ® U suture (Ethicon) was placed in the prepared cut. The suture loops were lifted out of the incision, and the sclera was perforated with a Superblade® (Medical Workshop). Next a Klöti Microstripper (Oertli) was introduced, with its infusion implement attached thereto. A planar contact lens was placed onto the cornea to facilitate inspection of the media and the eye bottom. The microstripper was set to work going round in small circular movements for a period of 15 minutes, whereby 20 ml of liquid were aspired through the instrument.

When the central portion of the vitreous humor had been cut away a thin Silastic ® tube (Dow Corning Corp.Med.Prod.), stabilized interiorly with a cannula of 0.6 mm interior diameter, was introduced through the sclerotomy. Injection of the crosslinked hyaluronic acid gel (produced according to Examples 1 and 2 resp.) was then initiated. Gradually increasing pressure in the vitreous humor caused thin liquid to run off along the outside of the Silastic ® tube through the sclerotomy. Injection of the gel through the thin tube proceeded smoothly, without any problems. When 0.6 to 0.7 ml of gel had been injected the sclerotomy was closed while the Silastic ® tube was being removed. The conjunctival flap was fastened with 6-0 Catgut Plain (Davis+Geck).

All in all, 22 eyes were operated on, and all of them were observed during a four-week period. After this, 14 eyes were observed during another five months. The intraocular pressure was normal during the entire postoperative period. All eyes healed, and the blood was absorbed so that after four weeks the retina was contiguous in all cases and the vitreous humor was entirely clear. No side reactions were observed to occur in the form of either inflammatory irritations, cataracts or synechiae. At the end of the experimental period, i.e. after six months, hyaluronic acid gel could still be detected in the vitreous humor of the animals.

We claim:

1. In the retinal surgery method in which a viscous fluid is introduced into an intraocular space enclosed between a rear boundary formed by the retina and a frontal boundry normally formed by the lens and the ciliary body, so that the pressure applied on the receptor layer by the viscous fluid, conjointly with any remaining portions of natural humor, will cause the receptor layer to lie in contact with the pigment epithelial layer for a period of time sufficient for healing, the improvement comprising that said viscous fluid contains a sterile and pyrogen-free gel of cross-linked hyaluronic acid.

2. In the method following vitrectomy in which a viscous fluid is introduced into an intraocular space enclosed between a rear boundary formed by the retina and a frontal boundary normally formed by the lens and the ciliary body or in aphatic eyes formed by the cornea, in a manner such that said viscous fluid, together with any remaining natural vitreous humor, will fill out all of said intraocular space, the improvement comprising that said viscous fluid contains a sterile and pyrogen-free gel of crosslinked hyaluronic acid.

3. A method according to claim 1 in which the gel has a dry solids content of from 0.1 to 50% by weight.

4. A method according to claim 2 in which the gel has a dry solids content of from 0.1 to 50% by weight.

5. A method according to claim 1 in which the gel has a dry solids content of from 0.2 to 25% by weight.

6. A method according to claim 2 in which the gel has a dry solids content of from 0.2 to 25% by weight.

7. A method according to claim 1 in which cross-linking of hyaluronic acid has been effected with at least one reagent forming ether or amide bridges to the hyaluronic acid molecules.

8. A method according to claim 7 in which said reagent is a bifunctional or polyfunctional epoxide, or a corresponding halohydrin or epihalohydrin or halide.

9. A method according to claim 2 in which cross-linking of hyaluronic acid has been effected with at least one reagent forming ether or amide bridges to the hyaluronic acid molecules.

10. A method according to claim 9 in which said reagent is a bifunctional or polyfunctional epoxide, or a corresponding halohydrin or epihalohydrin or halide.

11. A method according to claim 2 wherein the cross-linking reaction has been carried out with an amount of cross-linking agent equal to a molar ratio of 0.03 to 4.0 per disaccharide repeating unit of the hyaluronic acid molecule.

12. A method according to claim 3 in which cross-linking of hyaluronic acid has been effected with at least one reagent forming ether or amide bridges to the hyaluronic acid molecules.

13. A method according to claim 12 in which said reagent is a bifunctional or polyfunctional epoxide, or a corresponding halohydrin or epihalohydrin or halide.

14. A method according to claim 3 wherein the cross-linking reaction has been carried out with an amount of cross-linking agent equal to a molar ratio of 0.03 to 4.0 per disaccharide repeating unit of the hyaluronic acid molecule.

15. A method according to claim 4 in which cross-linking of hyaluronic acid has been effected with at least one reagent forming ether or amide bridges to the hyaluronic acid molecules.

16. A method according to claim 15 in which said reagent is a bifunctional or polyfunctional epoxide, or a corresponding halohydrin or epihalohydrin or halide.

* * * * *